US006189533B1

(12) United States Patent
Simon et al.

(10) Patent No.: US 6,189,533 B1
(45) Date of Patent: Feb. 20, 2001

(54) ENDOTRACHEAL INTUBATION DEVICE

(76) Inventors: James S. Simon; Robert A. Simon, both of P.O. Box 726, Tiburon, CA (US) 94920

( * ) Notice: Under 35 U.S.C. 154(b), the term of this patent shall be extended for 0 days.

(21) Appl. No.: 09/368,640

(22) Filed: Aug. 4, 1999

(51) Int. Cl.⁷ .................................................. A61M 16/00
(52) U.S. Cl. ................................ 128/207.14; 128/207.15; 128/200.26
(58) Field of Search ....................... 128/207.14, 207.15, 128/200.26

(56) References Cited

U.S. PATENT DOCUMENTS

| 4,150,676 | * | 4/1979 | Jackson | 128/207.15 |
| 5,285,778 | * | 2/1994 | Mackin | 128/207.15 |
| 5,287,848 | * | 2/1994 | Cubb et al. | 128/200.26 |
| 5,329,940 | * | 7/1994 | Adair | 128/200.26 |
| 5,607,386 | * | 3/1997 | Flam | 600/120 |
| 5,819,727 | * | 10/1998 | Linder | 128/200.26 |
| 5,941,816 | | 8/1999 | Barthel et al. . | |

* cited by examiner

Primary Examiner—John G. Weiss
Assistant Examiner—V. Srivastava
(74) Attorney, Agent, or Firm—Morrison & Foerster, LLP

(57) ABSTRACT

The present invention relates to an endotracheal intubation device that will allow visualization of the airway of a patient during intubation simultaneous with suctioning ability to remove debris in the airway. The endotracheal intubation device includes a light source disposed to shine proximal to the distal end of an endotracheal tube and means for connection to a suction source. The light source may be built into the endotracheal tube or may consist of a lighted sleeve encasing a suction trocar. The light source may be disposed to shine axially or radially from the proximal end to the distal end of an endotracheal tube and may be fiberoptic or chemiluminescent in nature. The shape of the endotracheal tube may be adjusted either by use of a malleable suction trocar made out of a malleable material such as aluminum or by inclusion of a malleable wire within the tube.

10 Claims, 3 Drawing Sheets

ENDOTRACHEAL INTUBATION DEVICE

BACKGROUND OF THE INVENTION

1. Technical Field

This invention relates to medical instruments generally and more particularly to an endotracheal intubation device having a light source for illumination during intubation and a means for attaching the device to a suction source.

2. Description of Related Art

Endotracheal intubation is a medical procedure that is used to establish a secure direct path for air under emergency resuscitation conditions or during induction of general anesthesia.

A clear airway is often critical for resuscitation efforts. An endotracheal tube may be used by medical personnel to establish an airway during resuscitation. This is necessary because the airway can become obstructed, either by a foreign body or by fluid, blood, or tissues such as the patient's tongue. Additionally, a patient in a major arrest state is unable to move air and as a result death rapidly ensues in the absence of introduced oxygen through the airway.

During intubation, an endotracheal tube must be passed through the vocal cords. Often, lighting is inadequate and foreign bodies, fluids, blood, loose dentures, or a flaccid tongue may compromise visualization of the vocal cords.

Often during an intubation procedure, a practitioner holds a lighted endotracheal blade in one hand, to elevate the palate and improve visualization, and a suction tube in the other hand, to remove loose debris that may be blocking visualization. However, in order to introduce the endotracheal tube, the suction must be put aside, thereby compromising visualization.

The present invention is designed to overcome the aforementioned visualization difficulties during intubation. The present invention is an endotracheal intubation device containing a light source and having simultaneous suctioning ability, enabling a practitioner to apply suction to a patient's airway while at the same time visualizing the airway for insertion of the endotracheal tube. The light source is designed to shine proximal of the distal end of the endotracheal tube. The invention includes an endotracheal tube with a light source that is either fiberoptic or chemiluminescent in nature. One variation includes a suction trocar inside the endotracheal tube in which the trocar is encased in a light-emitting sleeve. The light source for the sleeve may be either fiberoptic or chemiluminescent in nature and the trocar may be made of a malleable material. One example of such a malleable material is aluminum. Another embodiment includes an endotracheal tube with a light source built in. The light source may be fiberoptic or chemiluminescent in nature and may shine either axially or radially from the proximal end toward the distal end of the endotracheal tube. The lighted endotracheal tube may include a connection to a suction source and a malleable wire for adjustment of the shape of the tube under emergency conditions such as cardiopulmonary resuscitation.

BRIEF SUMMARY OF THE INVENTION

The invention is an endotracheal intubation device that will allow rapid intubation of a patient by allowing an intubator to visualize the patient's airway while at the same time suctioning out debris that could compromise visualization.

Generally, the inventive endotracheal intubation device contains both a suction source and a light source. The light source is placed so that it shines proximal to the distal end of the endotracheal tube. The light source may be either fiberoptic or chemiluminescent in nature. It may be disposed to shine either axially or radially from the proximal end of the endotracheal tube towards its distal end.

The endotracheal intubation device may include a suction trocar encased in a lighted sleeve within an endotracheal tube, enabling an intubator to simultaneously visualize a patient's airway and suction out debris through the suction trocar. The light source for the lighted sleeve may be either fiberoptic or chemiluminescent in nature.

The endotracheal intubation device typically contains a suction trocar made out of a malleable material and encased in a lighted sleeve within an endotracheal tube, enabling an intubator to simultaneously visualize a patient's airway and suction out debris through the suction trocar. By bending the malleable trocar, an intubator may change the shape of the endotracheal tube. An example of a malleable material that may be used for construction of the trocar is aluminum.

The endotracheal intubation device may have the light source built into the endotracheal tube and disposed to shine light proximal to the distal end of an endotracheal tube. The light source of this invention may be either fiberoptic or chemiluminescent in nature and the light may be disposed to shine either axially or radially from the proximal end of the endotracheal tube towards its distal end. The invention may further include means for connection of the endotracheal tube to a suction source.

Finally, the inventive endotracheal intubation device preferably includes a ring of light-emitting material at the proximal end of an endotracheal tube as a light source. The light source may be either fiberoptic or chemiluminescent in nature. The invention may further include connection of the endotracheal tube to a suction source and may also further include a malleable wire within the endotracheal tube for adjusting the shape of the tube.

DETAILED DESCRIPTION OF THE INVENTION

Figure 1:
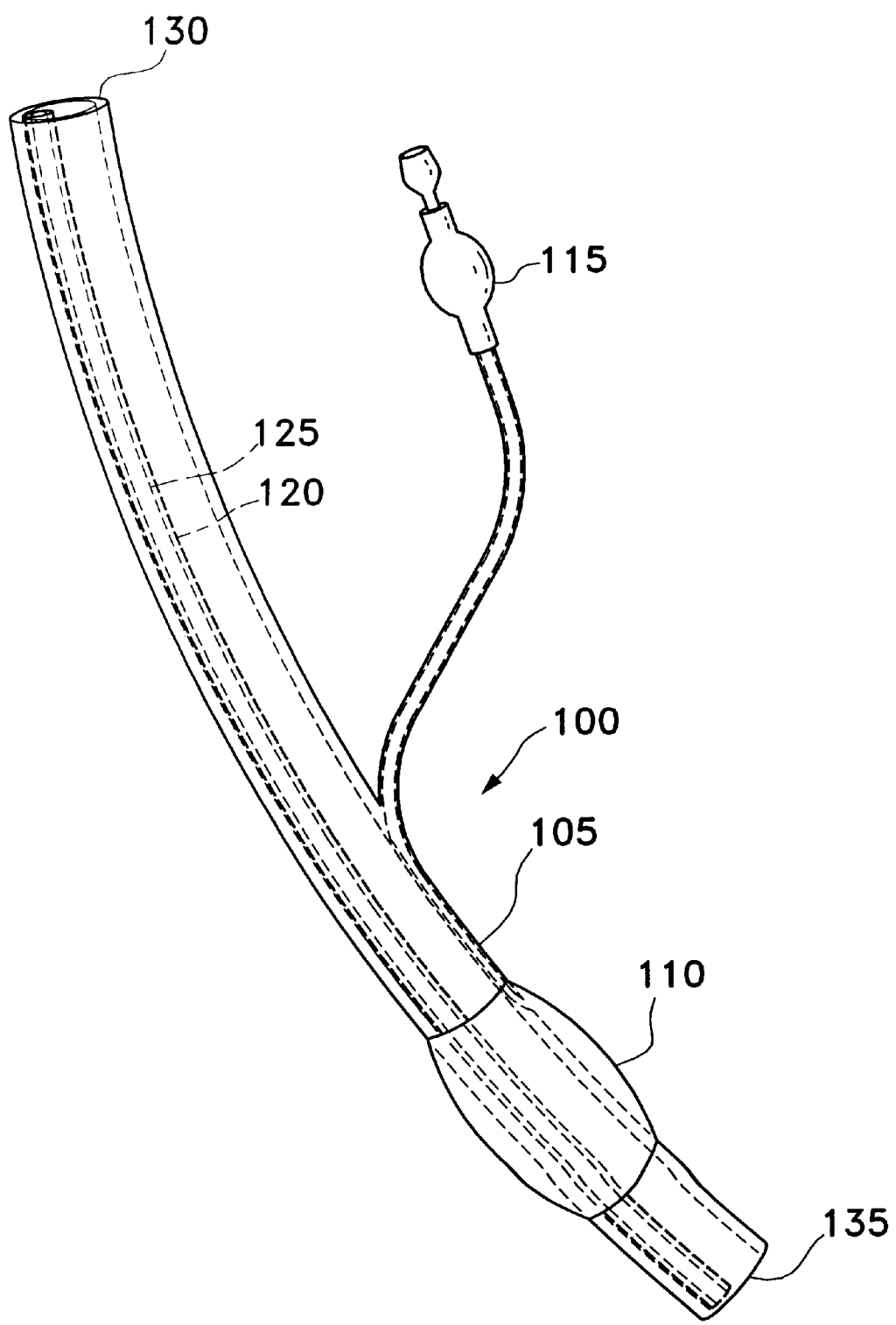
FIG. 1 is a perspective view of an endotracheal intubation device in accordance with the present invention having a suction trocar and a lighted sleeve for the suction trocar.

Referring to the drawings by numerals of reference, there is shown in FIG. 1 an endotracheal intubation device 100 in accordance with the present invention. The invention includes an endotracheal tube 105 having a proximal end 130 and a distal end 135. The endotracheal tube includes an air injection tube 115 and an inflatable cuff 110. The invention further includes a suction trocar 125 which fits within a lighted sleeve 120. The suction trocar may be connected to a suction source (not shown). A preferred light source for the trocar sleeve is fiberoptic. Another preferred light source for the trocar sleeve is chemiluminescent. The suction trocar 125 may be made of a malleable material. A preferred malleable material for the suction trocar is aluminum, although polymeric materials such as polyethylene or polypropylene may also be used.

Figure 2:
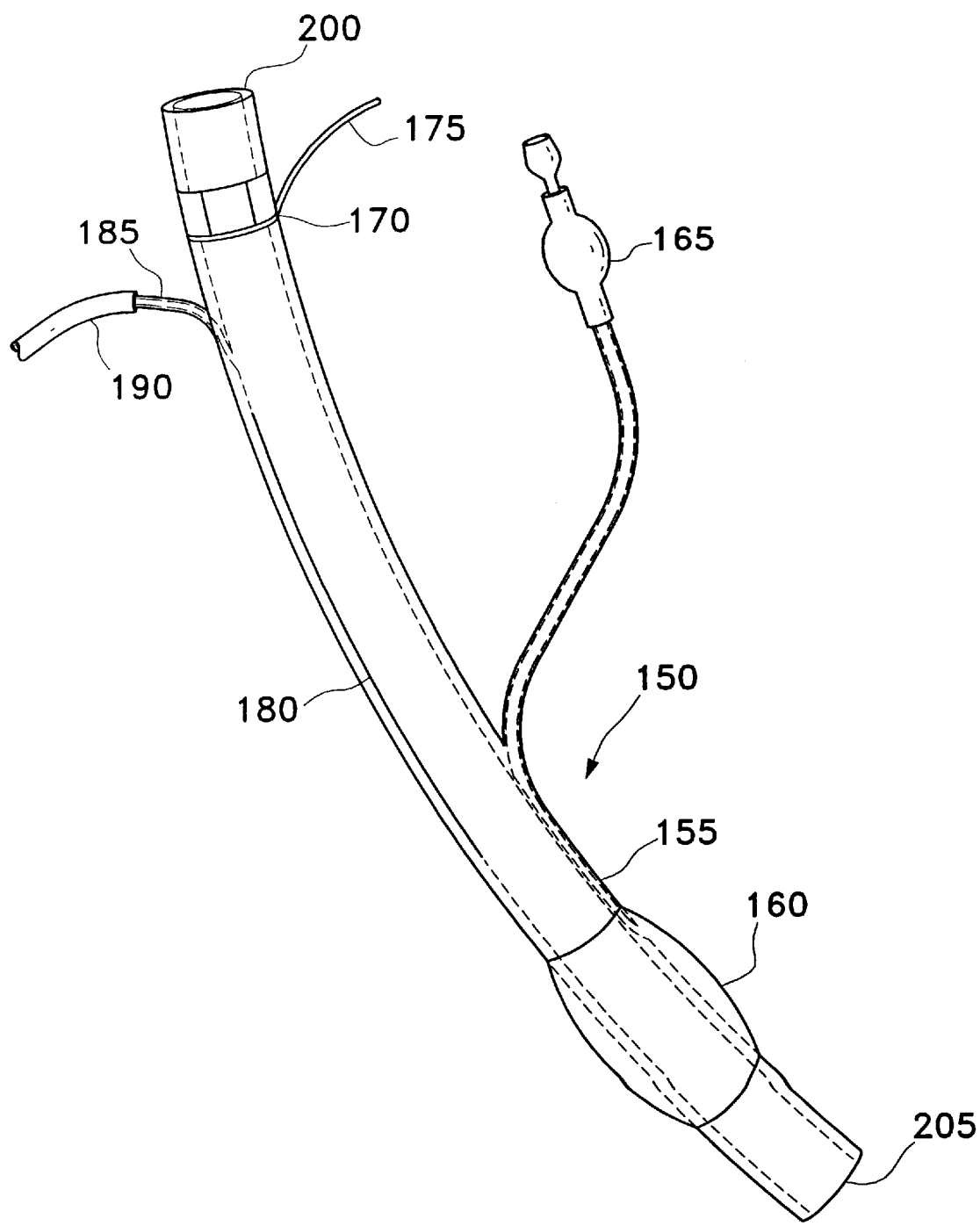
FIG. 2 is a perspective view of an endotracheal intubation device in accordance with the present invention having a light source built into the endotracheal tube and a separate connection to a suction source.

In FIG. 2 is shown another variation of an endotracheal intubation device 150 in accordance with the present invention. The invention includes an endotracheal tube 155 having a proximal end 200 and a distal end 205. The endotracheal tube includes an air injection tube 165 and an inflatable cuff 160. The invention further includes a light source 170 built into the endotracheal tube and a means for connecting the tube to a suction source 185. Flexible tubing 190 may be used to connect the endotracheal tube to a suction motor (not shown). The light source is disposed to shine axially or radially from the proximal end 200 to the distal end 205 of the endotracheal tube. A preferred shape for the light source is a ring of light emitting material. A preferred light source is fiberoptic. A fiberoptic power cord 175 may be used to connect the tube to a fiberoptic power source (not shown). Another preferred light source is chemiluminescent. The invention may further include a malleable wire 180 for adjusting the shape of the endotracheal tube.

Figure 3:
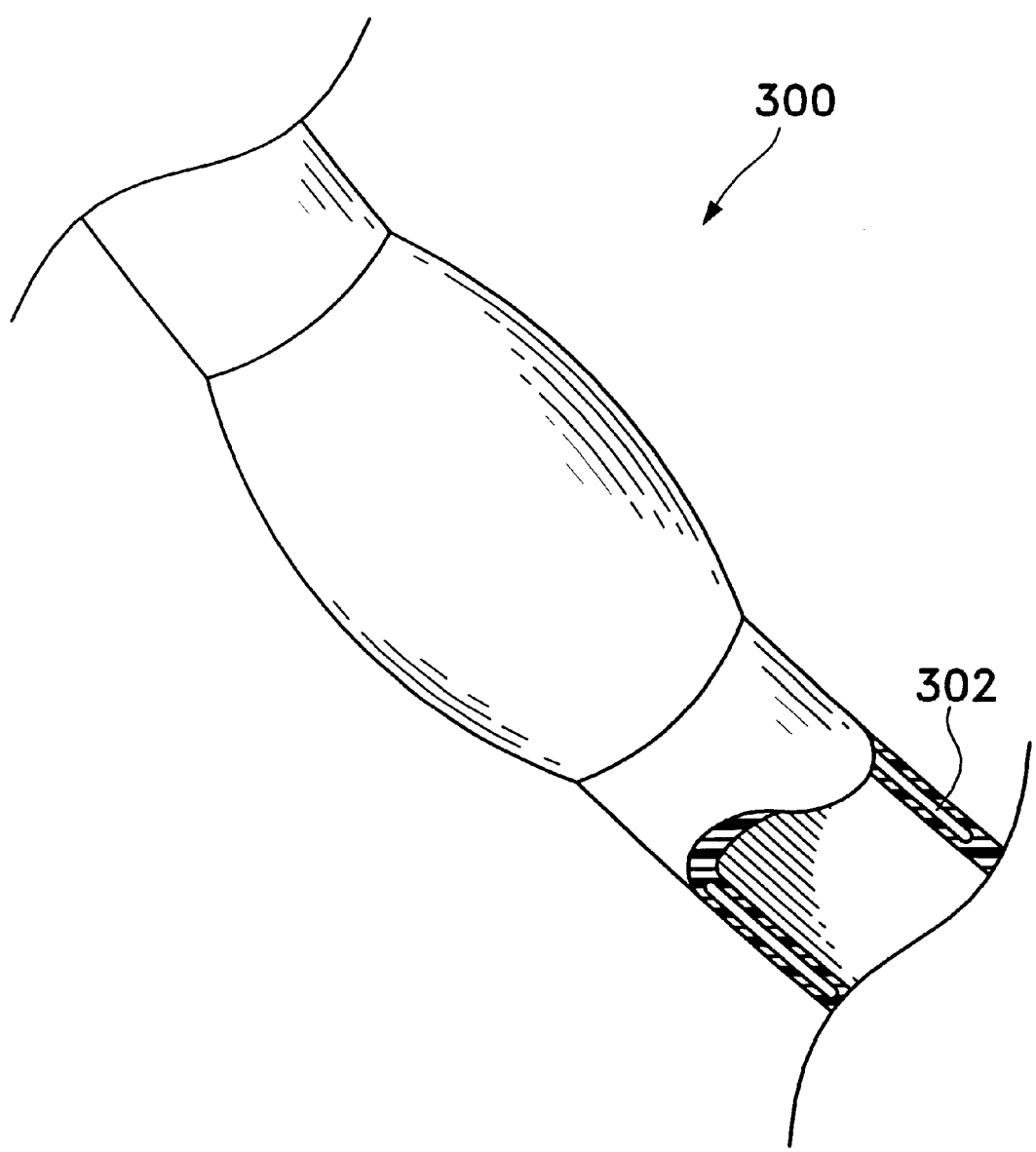
FIG. 3 is a perspective view of an endotracheal intubation device in accordance with the present invention having a chamber for inclusion of a chemiluminescent liquid, gel, or solid.

FIG. 3 shows another variation 300 of the invention. This variation includes a chamber 302 for inclusion of a chemiluminescent liquid, gel, or solid. A preferred variation is the inclusion of an induced or catalyzed chemiluminescent material such as that sold in Cyalurone "Lightsticks." An example of a chemiluminescent reaction is:

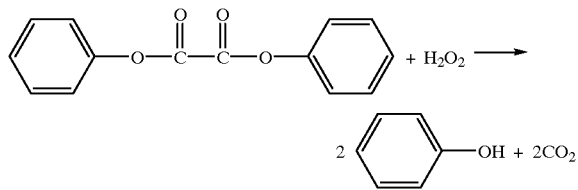

Modifications of the device described above that are apparent to one of ordinary skill in the art are intended to be within the scope of the claims that follow.

What is claimed is:

1. An endotracheal intubation device comprising:

a. an endotracheal tube having an endotracheal tube wall with a distal end; and b. a chemiluminescent light source, said light source composed of a chemiluminescent material contained within a ring-shaped, closed chamber built into the distal end of the endotracheal tube wall.

2. An endotracheal intubation device as in claim 1, further comprising attachment of the endotracheal tube to a suction source.

3. An endotracheal intubation device as in claim 2, wherein said attachment to the suction source comprises:

a. an adapter sleeve for connection to a suction source; and b. tubing for connection to a suction motor.

4. An endotracheal intubation device as in claim 1, further comprising a suction trocar.

5. An endotracheal intubation device as in claim 4, wherein said suction trocar is made out of a malleable material.

6. An endotracheal intubation device as in claim 5, wherein said malleable material is aluminum.

7. An endotracheal intubation device as in claim 4, further comprising a sleeve for the suction trocar, wherein the sleeve contains a light emitting material.

8. An endotracheal intubation device as in claim 1, further comprising a malleable wire for adjusting the shape of the tube.

9. An endotracheal intubation device as in claim 1, wherein said chemiluminescent material is a gel, liquid, or solid.

10. An endotracheal intubation device as in claim 7, wherein said chemiluminescent material is a gel, liquid, or solid.

* * * * *